US012642683B2

(12) United States Patent
Hoffeins

(10) Patent No.: US 12,642,683 B2
(45) Date of Patent: Jun. 2, 2026

(54) COMPRESSION GARMENT SET

(71) Applicant: medi GmbH & Co. KG, Bayreuth (DE)

(72) Inventor: Peter Hoffeins, Bayreuth (DE)

(73) Assignee: medi GmbH & Co. KG, Bayreuth (DE)

( * ) Notice: Subject to any disclaimer, the term of this patent is extended or adjusted under 35 U.S.C. 154(b) by 136 days.

(21) Appl. No.: 18/504,988

(22) Filed: Nov. 8, 2023

(65) Prior Publication Data

US 2024/0164932 A1      May 23, 2024

(30) Foreign Application Priority Data

Nov. 17, 2022    (EP) ..................................... 22020565

(51) Int. Cl.
A61F 5/30                (2006.01)
(52) U.S. Cl.
CPC ...................................... A61F 5/30 (2013.01)
(58) Field of Classification Search
CPC .......... A61F 13/10; A61F 13/08; A61F 13/06; A61F 13/062; A61F 13/066; A61F 13/061; A61F 5/0111; A61F 5/0127; A61F 13/069; A61F 5/30; A61F 13/063; A61F 13/064; A41B 11/10
See application file for complete search history.

(56) References Cited

U.S. PATENT DOCUMENTS

| | | | | |
|---|---|---|---|---|
| 2,296,207 | A | * 9/1942 | Kittinger ................... | A61F 7/02 |
| | | | | 604/307 |
| 5,823,195 | A | * 10/1998 | Shook ....................... | A61F 5/30 |
| | | | | 128/893 |
| 11,839,570 | B1 * | 12/2023 | Solotoff .................. | A61F 13/08 |
| 2004/0116866 | A1 * | 6/2004 | Gorman ................ | A61M 37/00 |
| | | | | 604/93.01 |
| 2015/0025435 | A1 * | 1/2015 | Sherman ................ | A41B 11/02 |
| | | | | 2/239 |

FOREIGN PATENT DOCUMENTS

| | | | |
|---|---|---|---|
| DE | 4104930 C2 * | 5/2000 | .......... A61F 13/066 |
| DE | 102013022088 | 6/2015 | |
| DE | 102019212740 | 2/2021 | |
| WO | WO-2023053038 A1 * | 4/2023 | ............. A42B 3/064 |

* cited by examiner

*Primary Examiner* — Ophelia A Hawthorne
(74) *Attorney, Agent, or Firm* — Rimon PC

(57)                ABSTRACT

The invention relates to a compression garment set for applying compression to a body part consisting of at least one compression article as well as at least one pressure pad pertaining to the compression article, wherein in the wearing position of the compression garment set pressure pad comes to lie under the compression article, and wherein the pressure pad has at least one adhesive surface a side directed towards the wearer in the wearing position so that the pressure pad can be positioned on the skin of a wearer detached from the compression article.

20 Claims, 8 Drawing Sheets

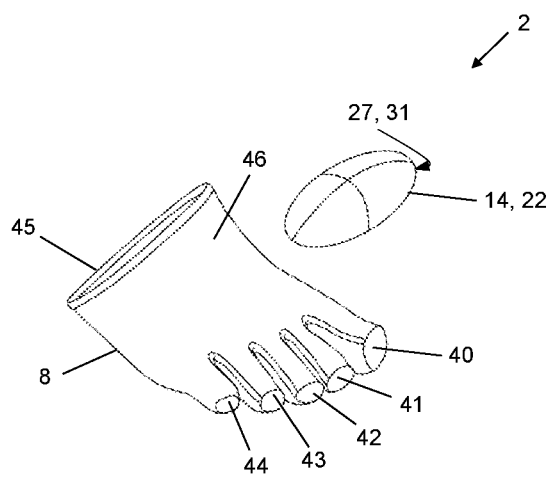
FIG. 2A
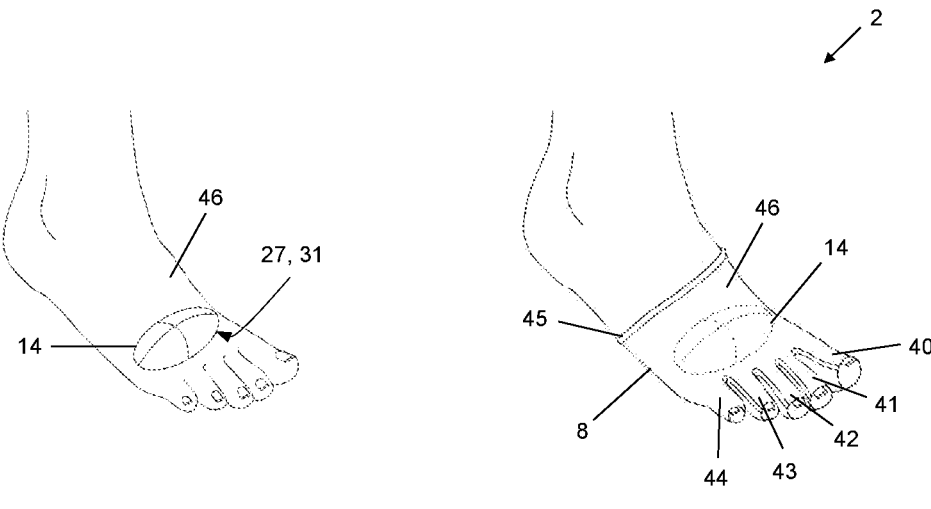
FIG. 2B          FIG. 2C

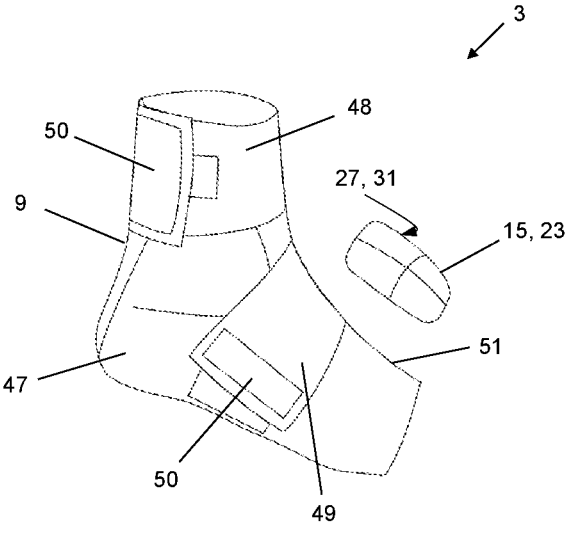
FIG. 3A
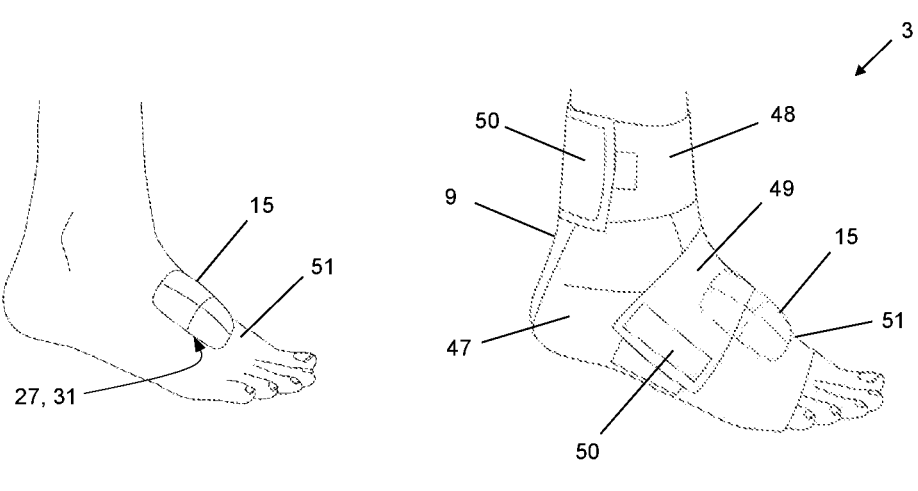
FIG. 3B                    FIG. 3C

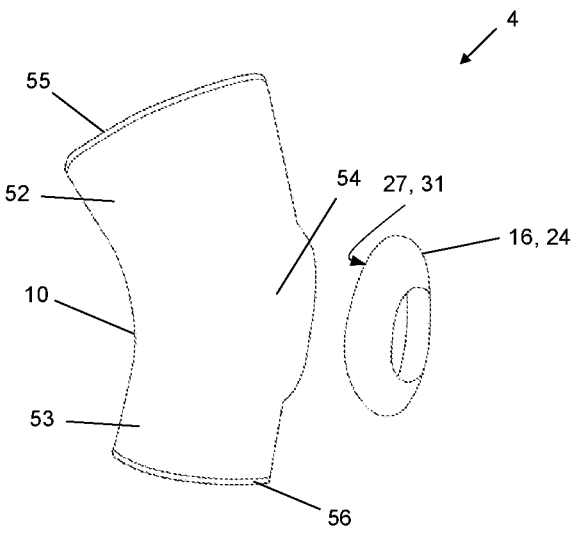
FIG. 4A
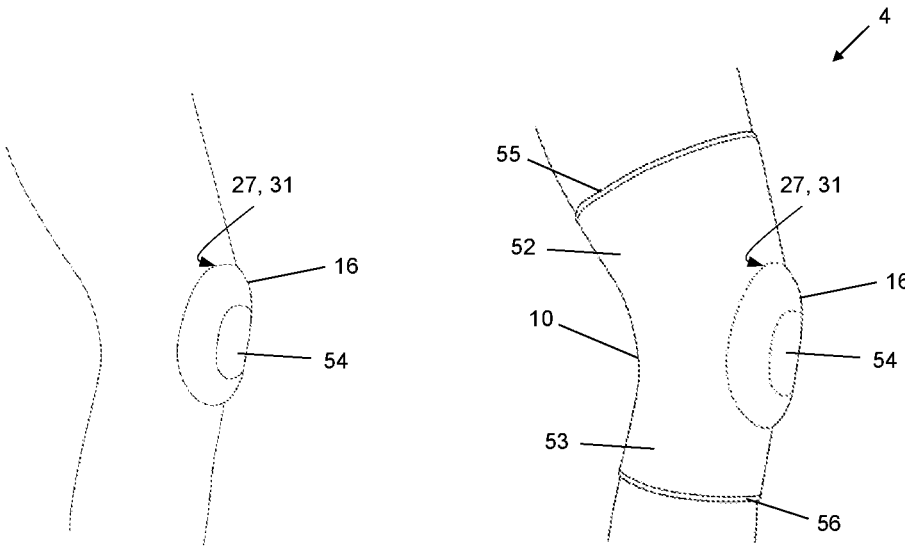
FIG. 4B                                                  FIG: 4C

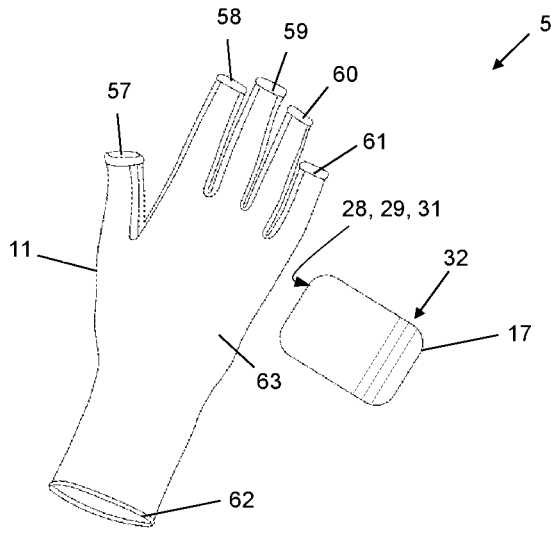
FIG. 5A
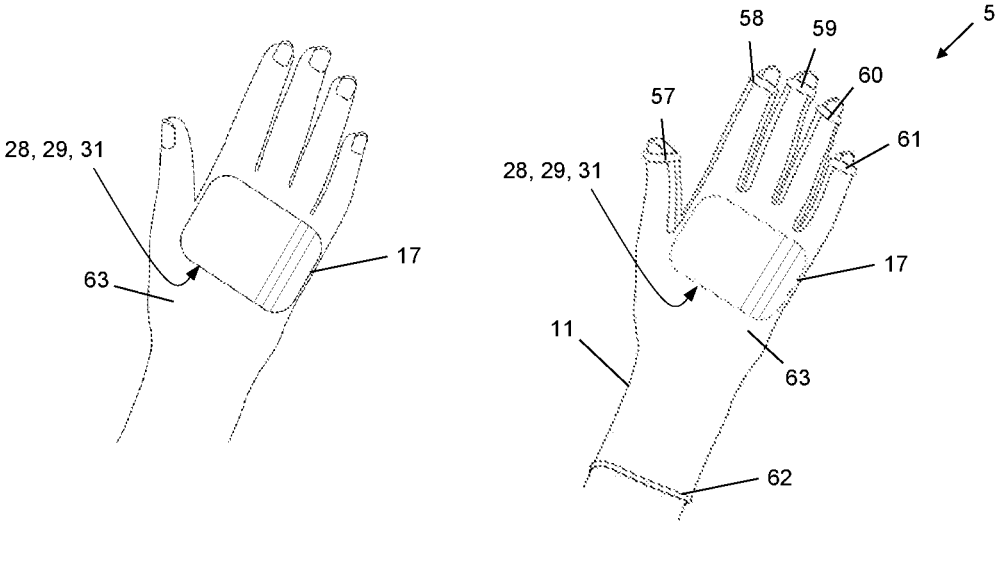
FIG. 5B                                          FIG. 5C

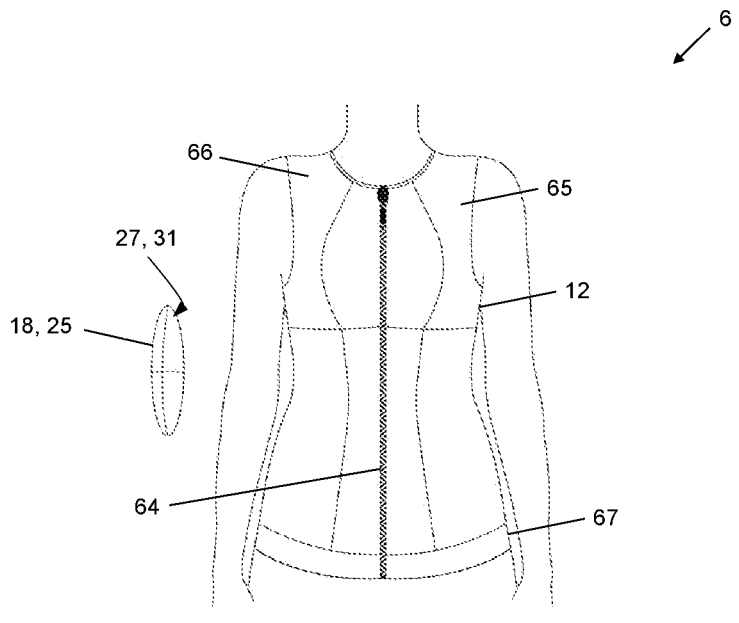
FIG. 6A
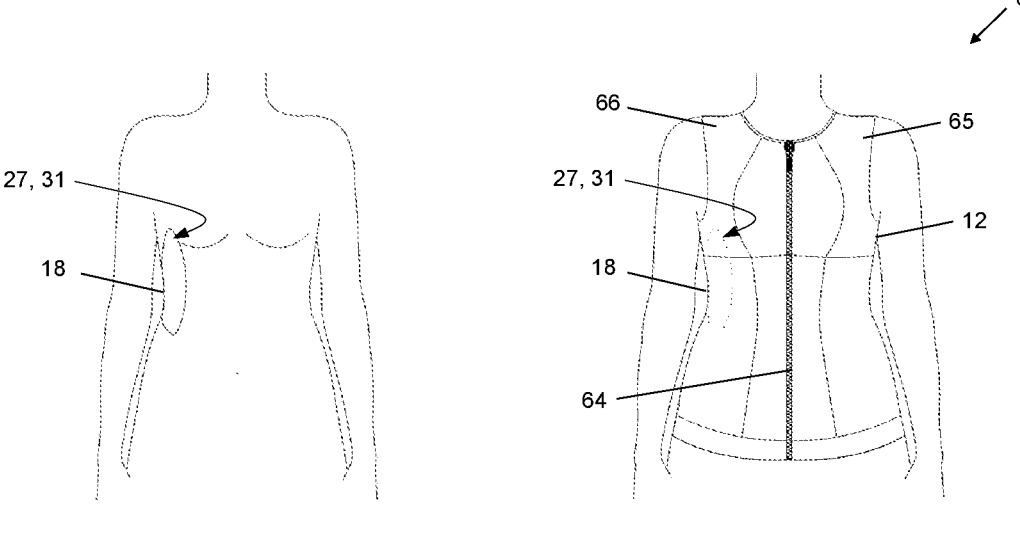
FIG. 6B                                    FIG. 6C

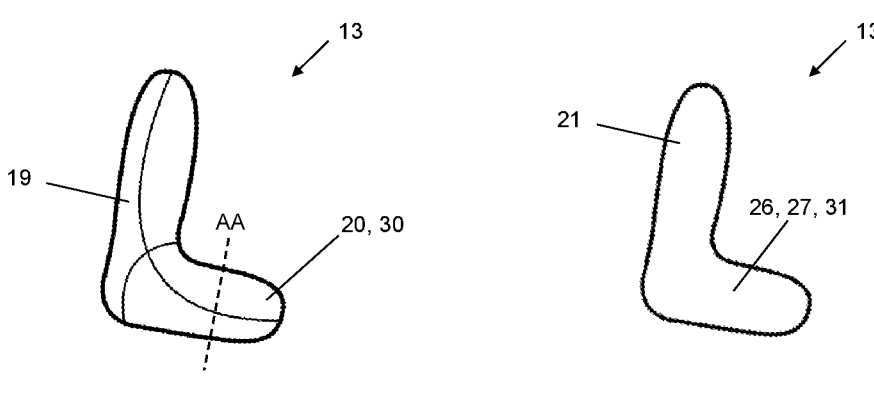
FIG.7A                    FIG. 7B
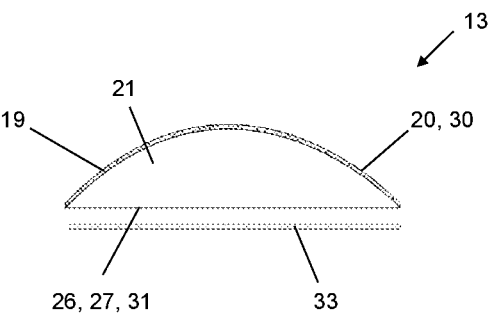
FIG. 7C
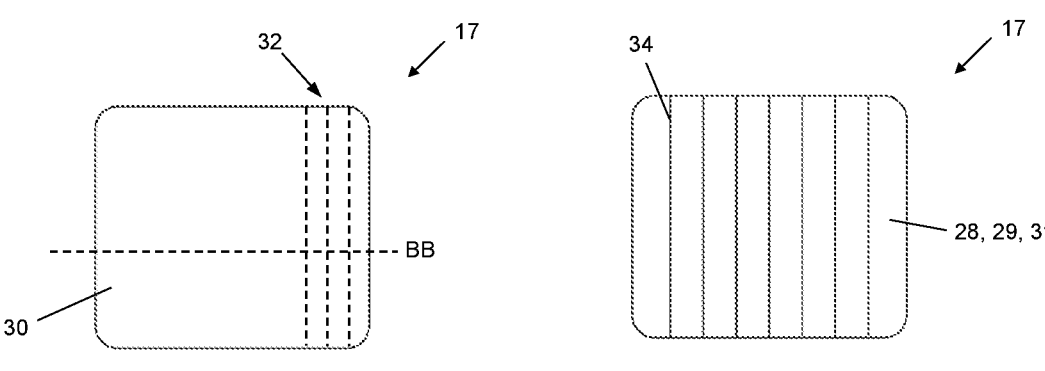
FIG.8A                    FIG. 8B

COMPRESSION GARMENT SET

CROSS-REFERENCE TO RELATED APPLICATIONS

This application claims priority to European Patent Application 22020565.2, filed on Nov. 17, 2022, the contents of which are incorporated herein by reference in its entirety as if set forth herein.

BACKGROUND

The present invention relates to a compression garment set for applying compression to a body part consisting of at least one compression article and at least one pressure pad pertaining to the compression article.

Such articles for applying compression to a body part are in particular configured in the form of stockings, preferably in the form of half stockings or thigh-length stockings or, for example as panty hose for a leg and/or a foot of a wearer for a compression therapy. It is also known to provide gloves and toe caps with compression or, for example, to fabricate compression garments. The latter serve to apply compression to the thorax of a patient. For this purpose, the compression articles have at least one, preferably a plurality of compression areas which serve to apply pressure specifically to the body of a patient. The pressure applied to the body of a patient is in this case designated as compression. The aim of such compressive articles is to relieve the pressure on a damaged venous or lymph system of a patient particularly in a medical usage. As a result of the pressure supplied, increasing swelling of the limbs is avoided, the removal of venous blood and lymph is improved and the blood supply is increased. When these compressive articles are used in the sports area, these bring about an improvement in performance or an improved regeneration.

RAL-GZ 387 of the Quality Mark Association exists for the manufacture, in particular for the measurement and quality assurance of compressive articles, in particular of knitted arm or leg stockings. From the test determinations of the RAL it can be deduced how, for example, the pressure of a compression stocking on a leg is to be determined. Testing on the HOSY measuring device, in particular compression testing device (Hohenstein Institute) is proposed as measurement means.

In addition to the previously described compressive articles for compression therapy, in particular for lymph or oedema therapy, compressive bandages are also known, for example, in the form of ankle or knee joint bandages which usually consist of a textile tubular and preferably compressive base body. The knee bandage is in particular configured as a patellar tendon bandage.

The patellar tendon is part of the knee joint and fulfils an important function in the stabilization and mobility of the knee joint. It connects the thigh muscle quadriceps femoris to the shin via the patella. The entire force effect of the thigh muscle on the lower thigh is thus transmitted via the patellar tendon which is a very narrow tendon. In particular when bending and stretching the knee, this therefore results in a stressing of the tendon. When the knee joint is under high loading such as occurs during sport, for example, or as a result of incorrect loading, this can result in an inflammation of the patellar tendon which is frequently manifest as pain in the knee, in particular when climbing stairs or going downhill. Sportsmen who make jerky or abrupt movements in their sport are most affected.

Now it is further known to equip the initially described compression articles for compression therapy with so-called pressure pads, in particular pressure bodies. These serve to apply additional pressure to a desired point or a certain area. Equally by using such pressure pads in compression articles, a uniform pressure distribution can also be achieved. In particular, a circularly uniform pressure distribution is a prerequisite for effective compression therapy. According to the Laplace law, the pressure is proportional to the tension of the compression material but inversely proportional to the radius of the fabric located thereunder. Thus, for example, according to the Laplace law, the pressure applied to a protuberance such as the Achilles tendon or the tibial crest is higher than to a flat surface. In order to obtain a uniform pressure, small radii such as, for example, to the right and left of the Achilles tendon, are now cushioned due to the arrangement of the pressure pads, in particular in the form of pressure pads. As a result, pressure damage can be avoided, a uniform pressure distribution can be produced and in addition, healing can be improved.

When these pressure pads are arranged on the compressive base bodies of the previously mentioned compressive bandages, they also serve here to apply pressure locally to a body part. When the bandage is configured, for example, as a knee bandage, this serves to apply pressure specifically to the patellar tendon. As a result of this pressure, the knee pain is avoided, or at least significantly reduced. A plurality of compression articles for applying compression to a body part, which in particular additionally comprise a pressure pad, are known from the prior art.

Such a compression article, in particular in the form of a compression stocking, is known, for example, from EP 1 391 190 B1.

The compression stocking here is formed from an elastic woven, knitted or crocheted fabric. A compression body configured as a pressure pad made of an elastic material and having a recess for accommodating a patella of a knee joint is arranged in the area of a knee joint between the compression stocking and the knee joint. This pressure pad is firmly attached to the inner side of the compression stocking.

A further compression article configured as an ankle bandage is known, for example, from EP 2 594 233 B1.

The orthopaedic bandage arrangement for an ankle comprises a sock-like knitted base body and a belt part which can be connected to the knitted part. The belt part comprises an elongate belt base body wherein at least one belt section protrudes from this, which extends on the outside of the foot in the worn state of the bandage arrangement. The knitted base body can now have at least one pressure pad extending over the ankle in the worn state. The pressure pad thereby increases the orthopaedically effective function of the knitted base body or the knitted part and thus the bandage arrangement overall. The pressure pad is in this case also incorporated in the knitted base body of the bandage arrangement.

Finally DE 20 2014 011 197 U1 discloses a compression article, in particular a knee brace and a pressure pad system for this.

The knee brace here comprises a knitted body. A first tension strap is provided on the front side which runs around the knitted body only in sections and extends over at least one pressure pad. A second tension strap is provided on the rear side and offset in terms of height to the first tension strap, which also runs around the knitted body only in sections. Both straps are configured for adjusting a pressure on the pressure pad, wherein the first tension strap extends directly over the pressure pad. Preferably a plurality of pressure pads are provided. The pressure pads are here accommodated in pockets attached to the knitted body, wherein the pockets can be partially open so that the pressure pads can optionally be removed and if needed, can be replaced by pressure pads designed to the somewhat harder or softer in terms of material. Alternatively the pockets can be closed on all sides so that it is not possible to remove or exchange the pressure pads.

A disadvantage of this configuration of the compression article and the relevant pressure pads is that the pressure pads are fastened in or on the compression article regardless of at which positions or for which orthopaedic purposes. The pressure pads are hereby integrated in the compression articles, in particular in the knitted base body thereof so that a positionally fixed connection of the pressure pad to the compression article is obtained.

This connection of the pressure pad to the compression article results in an increased process and processing expenditure. As described in the prior art, the pressure pads are usually accommodated in pockets attached to the compression article. In addition to the material costs, in particular the manufacturing costs, in particular the gluing-on, welding-on or sewing-on of the pocket material to the compression articles must also be taken into account to form these pockets. In addition, the pressure pad must be introduced manually into the pocket which also incurs costs.

It also proves to be disadvantageous that if the pressure pad is firmly connected to the compression article, the compression article can only be worn together with the pressure pad. It is not possible to upgrade or downgrade the compression article, i.e. to use the compression article with or without pressure pads, depending on the course of the compression therapy. Thus, for example, in the case of a positive course of therapy after which no additional pressure body is required, a new compression article must be acquired. This is associated with additional costs for the patients.

In addition, this also results in the disadvantage that the location, i.e. the position of the pressure pad on the compression article cannot be varied, i.e. is fixedly determined. That is to say, a fit of the compression article after fabrication can no longer be optimized or corrected.

If, for example, the position of the pressure pad on the compression article was incorrectly determined before fabricating the compression article, for example, due to inaccurate order details, this results in fabrication errors or manufacturing tolerances, for example, in a compression stocking so that this cannot be worn by the user. The compression stocking must be fabricated anew which results in additional costs for the patient or in the case of a complaint, for the manufacturer of the compression article. The locally increased compression effect due to the pressure pad would then be applied to an incorrect body position of a patient.

Another disadvantage which also exists even when the pressure pad is configured to be detachable from the compression article, in particular removable from a pressure pad pocket, is that the pressure pad shape or geometry is predefined by the pocket. As a result, it is not possible to vary between several pad in pressure shapes, particular during compression therapy, exactly as in the case of a pressure pad arranged firmly on the compression article.

However, even regardless of the manner in which the pressure pads are fastened to the compression articles, i.e. detachably or non-detachably, merely the fact that the pressure pads are arranged on the compression articles brings with it the disadvantage that putting on and taking off the compression article is thereby made more difficult. It is generally known that compressive articles, in particular compressive stockings or hosiery are already difficult to put on per se. The arrangement of further components, in particular one or more pressure pads, makes putting-on and taking-off more difficult as a result of their shapes and materials. The pressure pads are mostly fabricated from a rigid material. The wearing comfort which also comprises the ease of putting on and taking off the compression article deteriorates in any case as a result.

It is therefore the object of the present invention to provide a compression garment set which avoids the disadvantages from the prior art, in particular significantly improves the accuracy of fit and the wearing comfort of the compression garment set.

SUMMARY

According to one exemplary embodiment, the compression garment set according to the invention for applying compression to a body part consists of at least one compression article as well as at least one pressure pad pertaining to the compression article, wherein in the wearing position of the compression garment set the pressure pad comes to lie under the compression article, and wherein the pressure pad has at least one adhesive surface on a side directed towards the wearer in the wearing position so that the pressure pad can be positioned on the skin of a wearer detached from the compression article. That is to say, the pressure pad has an adhesive, preferably slightly sticky, adhesive, in any case, self-adhesive surface. This is in particular configured in such a manner that the pressure pad itself, i.e. without additional assistance such as, for example, a support belt which surrounds the pressure pad and the body part of the wearer on all sides, adheres to the skin of a wearer. In addition, the adhesive surface is preferably configured in such a manner that the pressure pad can be detached again from the skin of a wearer. That is to say again that no external means such as solvents, for example, are required to remove the pressure pad from the skin of a wearer. Particularly preferably the pressure pad, in particular the adhesive surface, is configured in such a manner that this can be used multiple times. This therefore preferably comprises a reusable pressure pad.

According to a second exemplary embodiment, the at least one pressure pad is configured in such a manner that this has at least one support element for at least one pressure pad element attached thereto on a side facing away from the wearer in the wearing position. The at least one support element is preferably fabricated in this case from a very thin, tear-resistant support film with a low-friction surface on the outer side e so that the pressure pad has enhanced sliding properties on the side facing the compression article. Pulling on the compression article is considerably facilitated by the low-friction surface of the outer side of the pressure pad. The pressure pad thus additionally fulfils the purpose similarly to a pull-on aid for compression stockings or bandages.

According to a third exemplary embodiment, the at least one pressure pad or the at least one pressure pad element consists of an elastic or plastically deformable plastic material. The plastic material can in this case have different material properties, in particular degrees of hardness. Particularly preferably the at least one pressure pad element consists of a silicone with an adhesive surface so that the pressure pad element itself forms at least one adhesive surface. Alternatively the at least one adhesive surface can be formed by an adhesive layer applied to the pressure pad or the at least one pressure pad element. The adhesive layer can in this case be applied over the entire surface or only locally at one or more positions of the pressure pad.

According to a further exemplary embodiment, the pressure pad or the at least one pressure pad element has a geometry adapted to the anatomy of the body part in the wearing position on the side directed towards the wearer in the wearing position. In this case, the pressure pad or the at least one pressure pad element is formed on the side substantially flat, convex or concavely curved. That is to say, on the side facing the wearer the pressure pad has only very few, preferably no protrusions or recesses. As a result the pressure pad can be positioned on the skin of a wearer over the entire surface, i.e. with the largest possible area. The best possible hold of the pressure pad to the skin of a wearer is hereby achieved.

Alternatively the pressure pad or the at least one pressure pad element has at least one recess on the side directed towards the wearer in the wearing position or a plurality of adjoining or spaced-apart pressure pad elements are attached to the support element. The aim here is to form at least one transport canal for lymph fluid in the wearing position below the pressure pad. As a result, the pressure pad can additionally be attached at body positions with narrow radii since the pressure pad, particularly when it is fabricated from a flexible material can then be deformed according to the predefined anatomy due to the at least one recess or due to the spaced-apart pressure pad elements.

Particularly preferably the least one pressure pad is substantially convexly curved on a side facing away from the wearer in the wearing position. The convex curvature of the pressure pad assists the uniform pressure distribution of the compression article located thereabove and arranged on the body part.

According to a further exemplary embodiment, the pressure pad has one or more cutting markings so that the pressure pad can be individually adapted in its shape. This can, for example, comprise one or more markings printed on the pressure pad, in particular lines. Alternatively these markings can be configured as perforations in the material of the pressure pad. As a result, the size of the pressure pad can be individually adapted to the body part of the wearer. This can be achieved with or without an external tool. In addition, the cutting markings can further comprise identifiers which refer to a size of the pressure pad or the body part, for example, size information such as S to XL or circumferential dimensions, for example in the dimensional units millimetres or centimetres.

According to a further exemplary embodiment, the compression garment set further comprises at least one cover element that can be detachably attached to the at least one adhesive surface of the pressure pad. As a result, the adhesive surface of the pressure pad in an exposed state is protected from contaminants. The detachable cover element is here preferably configured as plastic film which covers the entire adhesive surface. The pressure pad is preferably supplied with the cover element. This is removed by the user before use and attached again to the adhesive surface, i.e. after use. Preferably the set further comprises a means for cleaning the adhesive surface so that the at least one pressure pad can be reused. The means is preferably configured in such a manner that it releases oil and grease contaminants, dust, dirt, make-up, skin flakes, skin particles and hair from the adhesive layer without thereby damaging the adhesive layer.

Particularly preferably the compression article is a compressive stocking, in particular an arm or leg stocking with or without a hand or foot part, a compressive sock, a toe cap, a compressive glove, a bandage, an adjustable, in particular adaptive compression textile such as, for example, a so-called compression wrap, a compressive waistcoat or a compressive element of an orthesis.

Preferably the compressive pressures generated by the compression article are between 5 and 60 mm Hg, preferably between 10 and 45 mm Hg, particularly preferably between 15 and 25 mm Hg. The said compression values, in particular for compressive arm and leg stockings, can be determined by the measurement instructions and measurement methods described initially, in particular according to RAL-GZ 387 of the Quality Mark Association and using the HOSY measuring device (Hohenstein Institute).

The present compression garment set is characterized b a number of considerable advantages.

Due to the configuration of the compression garment set in such a manner that the pressure pad can be positioned detached, i.e. independently of the compression article on the skin of a wearer and can be fastened there, in particular due to its adhesive surface, it is possible that the pressure pad can be placed exactly at the previously specified local position preferably determined by a specialist, on the body part of a wearer. A one-hundred percent accuracy of fit is thereby achieved in relation to the arrangement and alignment of the pressure pad on the body part. Complaints in this regard, i.e. as a result of pressure pads incorporated incorrectly in a compression article, such as are known from the prior art so that the pressure pads come to rest incorrectly on the body part of a patient, can be completely eliminated.

In addition, due to the configuration of the compression garment set, it is possible to adapt this, in particular the compression article, individually to the course of the compression therapy. Thus, the compression garment set can be upgraded or downgraded. For example, it is possible to use the compression article with or without the pressure pad. In particular, a selection can be made from a plurality of pressure pads with different properties, in particular with regard to material, adhesive property and/or shape, depending on an accuracy of fit or a course of therapy. It is therefore no longer necessary to additionally exchange the compression article in addition to the pressure pad, as is known from the prior art.

A further advantage of the invention is the fact that it is significantly easier to put on and take off the compression garment set. The wearing comfort is thereby substantially enhanced. This specifically also includes the degree of difficulty of putting on and taking off the compression article. Compression articles, for example, compressive stockings which in most cases can basically only be put on and taken off with physical effort are now, according to the invention, no longer additionally provided with further components, i.e. with one or more pressure pads which make putting on and taking off more difficult. The pressure pad is namely according to the invention decoupled from the compression article. It is therefore no longer necessary to put on the compression article simultaneously with a pressure pad.

The possibility of using a closed compression article, for example, a circularly knitted compression stocking or seamlessly fabricated compression stocking on a flat bed knitting machine for such compression therapy with a pressure pad also constitutes an essential advantage. Hitherto no account was taken of these articles for the aforesaid compression therapy. The reason for this is that it is only possible with considerable expenditure and in some cases not possible at all to incorporate pressure pads into these articles which are closed in the circumferential direction.

Finally it should also be noted that the compression garment set according to the invention has a significant cost advantage compared with the previous compressive articles available in the market. It is no longer necessary to take measures on the compression articles in order to attach the pressure pad thereon. That is to say, pockets no longer need to be formed on the articles. During fabrication of the article the pressure pads no longer need to be placed manually in the pocket. The manufacturing costs are thereby significantly reduced.

The invention is explained hereinafter with reference to several exemplary embodiments and in conjunction with the appended drawings.

BRIEF DESCRIPTION OF THE DRAWINGS

In the figures:

FIGS. 2A to 2C show a second exemplary embodiment of a compression garment set according to the invention consisting of a compressive toe cap and a foot pressure pad also in a three-dimensional representation, namely in an unworn, partially worn and worn state, FIGS. 3A to 3C show a third exemplary embodiment of a compression garment set according to the invention consisting of a compressive and adjustable compression textile and a foot pressure pad in a three-dimensional representation, namely in an unworn, partially worn and worn state, FIGS. 4A to 4C show a fourth exemplary embodiment of a compression garment set according to the invention consisting of a compressive bandage and a knee pressure pad in a three-dimensional representation, namely in an unworn, partially worn and worn state, FIGS. 5A to 5C show a fifth exemplary embodiment of a compression garment set according to the invention consisting of a compressive glove and a hand pressure pad in a three-dimensional representation, namely in an unworn, partially worn and worn state, FIGS. 6A to 6C show a sixth exemplary embodiment of a compression garment set according to the invention consisting of a compressive waistcoat and thorax pressure pad in a three-dimensional representation, namely in an unworn, partially worn and worn state, FIGS. 7A to 7C show the ankle pressure pad according to the first exemplary embodiment of the compression garment set according to the invention comprising the compressive leg stocking from FIGS. 1A to 1C in a three-dimensional representation and in a sectional representation, FIGS. 8A to 8C show the hand pressure pad according to the fifth exemplary embodiment of the compression garment set according to the invention comprising the compressive glove from FIGS. 5A to 5C in a three-dimensional representation and in a sectional representation;

DETAILED DESCRIPTION

Figure 1A:
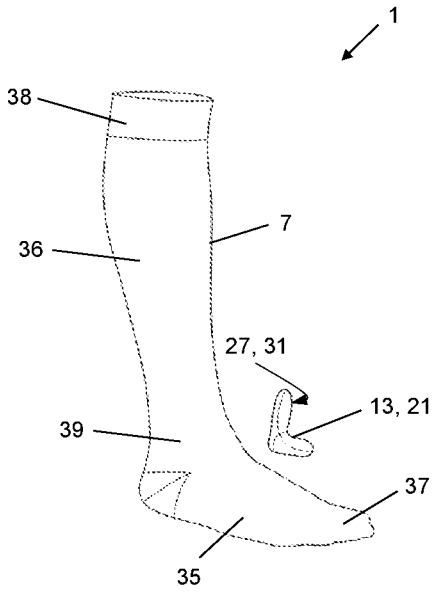
FIGS. 1A to 1C show a first exemplary embodiment of a compression garment set according to the invention consisting of a compressive leg stocking and an ankle pressure pad in a three-dimensional representation, namely in an unworn, partially worn and worn state.
Figure 1B:
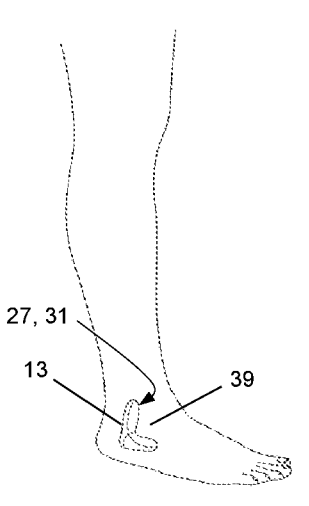
Figure 1C:
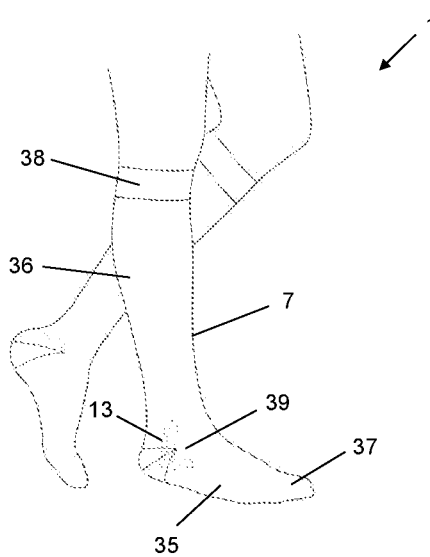

FIGS. 1A to 1C show a compression garment set 1 comprising a compression article in the form of a compressive leg stocking 7 and an ankle pressure pad 13. FIG. 1A shows the set 1 in an unworn state. In FIG. 1B the ankle pressure pad 13 is positioned on the foot of a wearer and fastened there. Finally FIG. 1C shows the leg stocking 7 and the pressure pad 13 in the worn state. FIGS. 1A to 1C thus illustrate pictorially the step-wise application of the compression garment set 1.

As can be seen in FIG. 1A, the compression article, i.e. the leg stocking 7, of the compression garment set is configured as a compressive half-stocking. In addition to a foot part 35, this comprises a calf part 36 preferably provided with a gradual pressure profile. The compressive pressure preferably decreases here from distal to proximal. The foot part 35 here comprises a closed toe region 37 and an area 39 surrounding the ankle. It is also possible that the foot part 35 is configured with an open toe region. In addition to the first section, preferably a knitted-in heel in the foot part 35, the half-stocking 7 has a collar section 38 at its upper end which is preferably configured as a double-layer collar. The stocking 7 here preferably consists of a circular- or flat-knitted compressive knitted part.

In addition to the compressive half-stocking 7, the compression garment set 1 now comprises an ankle pressure pad 13. The preferably L-shaped pressure pad 13 for an ankle area 39 now comprises according to the invention an adhesive surface 27 on the side 31 directed towards the wearer in the wearing position. As a result, as can be seen subsequently in FIG. 1A, the pressure pad 13 is positioned in a detached manner, i.e. independently of the half-stocking 7, on the skin of a wearer and fastened detachably there. For this purpose, as will be described subsequently in detail in FIGS. 7A to 7C, the ankle pressure pad 13 has a support element for at least one pressure pad element 21 attached thereon on a side facing away from the wearer in the wearing position. The pressure pad element 21 is preferably fabricated from an elastic or plastically deformable plastic material. Particularly preferably this consists of a silicone with an adhesive surface so that the pressure pad element 21 itself forms the adhesive surface 27 of the pressure pad 13. The ankle pressure pad 13, in particular the pressure pad element 21, further has a geometry adapted to the anatomy of the body part on the side 31 directed towards the wearer in the wearing position. Since the area 39 surrounding the ankle of a wearer is usually substantially flat or slightly concavely curved, the side 31 of the pressure pad 13 is preferably also configured to be flat or slightly convexly curved. Alternatively the side 31 can also be configured to be substantially concavely curved. The outer side of the pressure pad 13, i.e. the side facing away from the wearer in the wearing position is preferably configured to be convexly curved here.

FIG. 1B now shows a worn state of the compression garment set 1 in which only the ankle pressure pad 13 is positioned on the foot of a wearer, in particular in an ankle region 39. The adhesive surface 27 applied to the side 31 of the pressure pad 13 directed towards the wearer in the wearing position is here configured in such a manner that the pressure pad 13 can be positioned or fastened on the skin of a wearer in a detached manner, i.e. independently of the half-stocking 7. For this purpose, the adhesive surface 27 is preferably configured as a slightly sticky, adhesive, in any case self-adhesive surface. Thus, the pressure pad 13 sticks itself, i.e. without additional assistance, to the skin of the wearer. Naturally the adhesive property of the adhesive surface 27 is configured in such a manner that the ankle pressure pad 13 can be released from the skin of a wearer again. As a result of this configuration of the compression garment set 1 according to the invention, the angle pressure pad 1 can be placed precisely on the body part of a wearer.

FIG. 1C now shows the compression garment set 1 in a worn state, i.e. in addition to the positioned and applied ankle pressure pad 13, the leg stocking 7 with the foot part 35, the collar 38 and the toe region 37 is now also placed on the leg of the wearer. In this case, after the ankle pressure pad 13 has been positioned on the foot of the wearer, see FIG. 1B, the half-stocking 7 with the calf part 36 and the foot part 35 is pulled over the leg or the foot of the wearer and finally also over the pressure pad 13 arranged previously in the ankle region 39. As a result of this configuration of the compression garment set 1 according to the invention, the ease of putting on and taking off of the compression garment set 1 is substantially improved.

FIGS. 2A to 2C now show a compression garment set 2 with a compression article in the form of a compressive toe cap 8 and a foot pressure pad 14. FIG. 2A also shows the set 1 in an unworn state. FIG. 2B show the foot pressure pad 14 positioned on the foot of a wearer. In FIG. 2C the compressive toe cap 8 is now applied to the foot of a wearer in addition to the foot pressure pad 14. FIGS. 2A to 2C therefore also illustrate the gradual putting on of the compression garment set 2.

In FIG. 2A the compression article of the compression garment set 2 is configured as a compressive toe cap 8. In addition to an instep area 46 and a terminating edge 46, this has a plurality of toe sections 40 to 44 attached to the instep area 46. The compressive toe cap 8 serves to apply pressure to the forefoot area. In this exemplary embodiment, the compression article, i.e. the toe cap 8 is preferably also fabricated from a circular or flat-knitted compressive knitted part.

The compression garment set 2 further comprises the foot pressure pad 14. The preferably pad-shaped pressure pad 14 for the instep area 46 now has, according to the invention, an adhesive surface 27 on the side 31 directed towards the wearer in the wearing position. The pressure pad 14 can thereby be positioned a detached manner, i.e. independently of the to cap 8 on the skin of a wearer. For this purpose the pressure pad 14, like the pressure pad 13 according to FIG. 1A, also has a support element for at least one pressure pad element 22 attached thereto on a side facing away from the wearer in the wearing position. In this case, the pressure pad element 22 is preferably also formed from a silicone with an adhesive surface so that the pressure pad element 22 itself forms the adhesive surface 27. According to this exemplary embodiment, the foot pressure pad 14, in particular the pressure pad element 23, has a geometry adapted to the anatomy of the body part on the side 31 directed towards the wearer in the wearing position, in particular this is preferably configured to be flat or slightly concavely curved. The outer side of the pressure pad 14 on the other hand is preferably configured to be convexly curved.

FIG. 2B now shows a first worn state of the compression garment set 2. In this, only the foot pressure pad 14 is positioned on the foot, in particular on the instep area 46 of a wearer and firmly attached there. For this purpose, the pressure pad 14 which has the adhesive surface 27 on the side 31 directed towards the wearer in the wearing position, is positioned thereon or fixed there in the area of the instep 46. To this end, the adhesive surface 27 is likewise configured as a preferably slightly sticky, adhesive, in any case self-adhesive surface so that the pressure pad 14 sticks to the skin of the wearer without external assistance, i.e. is fixed there. As a result of this configuration of the compression garment set 2 according to the invention, the foot pressure pad 14 can be positioned exactly on the instep area 46 of the wearer and fixed there.

Finally FIG. 2C shows the compression garment set 2 in a second worn state, namely when both components of the set 2, i.e. the compression article 8 as well as the pressure pad 14 are put on the foot of the wearer. For this purpose, after the foot pressure pad 14 has been positioned on the foot of the wearer and fixed there, the compressive toe cap 8 with the terminating edge 45 and the plurality of toe sections 40 to 44 is pulled over the foot and over the pressure pad previously fixed there. It is therefore no longer necessary to pull a compression article with a pressure pad fixed thereon, as is known and usual from the prior art, together along the foot, in the specific case of application over a toe region as far as into a wearing position, namely until the pressure pad 14 is arranged in an instep area. The ease of putting on and taking off the compression garment set 2 according to the invention is therefore made considerably easier compared with the already known solutions.

FIGS. 3A to 3C now show a compression garment set 3 with a compression article configured as adjustable or adaptive compression textile 9 with a foot pressure pad 15. FIG. 3A again shows the set 3 in an unworn state. In FIG. 3B the foot pressure pad 15 is positioned on the wearer. According to FIG. 3C the compression garment set 3 is now put completely on the foot of the wearer.

As can be seen in FIG. 3A, the compression article of the compression garment set 3 is an adjustable or adaptable compression textile 9, in particular a so-called compression wrap, which consists of a base body 47 on which a plurality of, preferably two, straps 48, 49 are arranged. The straps 48, 49 each have a closure at their ends, preferably a Velcro surface 50, so that after they have been wrapped around the body part of the wearer, in particular around the foot and its instep area 51, the straps 48, 49 can be fixed to themselves or to the base body 47. The adjustable or adaptive compression textile 9 here preferably consists of a substantially inelastic woven fabric, in particular knitted fabric. This preferably has a multilayer structure and can be cut so that the compression textile 9 can be individually adapted to the body part of the wearer.

The compression garment set 3 now also comprises a pressure pad 15 with an adhesive surface 27 on the side 31 directed towards the wearer in the wearing position. As a result, as in exemplary embodiments previously, the pressure pad 15 can be positioned in a detached manner, i.e. independently of the compression article, in particular the compression textile 9, on the skin of a wearer, in particular in an instep area 51 and fixed there. For this purpose the foot pressure pad 15 is preferably also formed of a silicone with an adhesive surface, wherein a pressure pad element 23 is placed on a support element, in particular on a support film so that here also the pressure pad element 23 itself forms the adhesive surface 27 of the pressure pad 15. The pressure pad 15 is configured to be substantially flat or slightly concavely curved on the side 31 directed towards the wearer in the wearing position. The outer side of the pressure pad 15, i.e. the side facing away from the wearer in the wearing position, is preferably convexly curved here.

FIG. 3B now shows a worn state of the compression garment set 3 in which only the foot pressure pad 15 is positioned on the foot of a wearer, in particular in an instep area 51 and fixed detachably there. This is accomplished by the adhesive surface 27 which is attached to the pressure pad 15 on the side 31 directed towards the wearer in the wearing position. As in the exemplary embodiments previously, here also the pressure pad element 23 itself, i.e. its material, in particular the silicone used, forms the adhesive surface 27. As a result, the pressure pad 15 can be positioned on the skin of the wearer without additional assistance and can be fixed detachably there.

FIG. 3C now shows the compression garment set 3 in a worn state. In addition to the foot pressure pad 15 already positioned and applied in FIG. 3B, the adjustable compression textile 9, in particular the compression wrap, with the base body 47 and the plurality of straps 48, 49 is now put on the foot of the wearer, in particular in the instep area 51. In this case, the compression textile 9 extends over the pressure pad 15 and can thus apply pressure to this. The compression, in particular the compression strength, can in this case be adjusted individually by the straps 48, 49, this being according to the stretching of the straps 48, 49. The more the straps 48, 49 are stretched and then fastened to themselves or the base body 47 by means of the closures 50, the greater is the pressure applied to the body part and to the pressure pad 15. As a result of this configuration of the compression garment set 3 according to the invention, the ease of putting on and taking off is also substantially improved by this exemplary embodiment of the compression garment set 3. Due to the previous positioning and fixing of the pressure pad 15 on the body part, an exact positioning of the pressure pad 15 on the body part is ensured. The risk of slippage of the pressure pad 15 during application of the compression textile 9 is avoided. Also no slippage of the pressure pad 15 occurs during an adjustment of the compression by the plurality of straps 48, 49 since the pressure pad 15 is fixed to the body part of the wearer and not to the compression article as in the prior art.

FIGS. 4A to 4C now show a compression garment set 4 with a compression article in the form of a knee bandage 10 and a knee pressure pad 16. FIG. 4A shows the set 4 in an unworn state. In FIG. 4B the knee pressure pad 16 is positioned on the leg of a wearer. Finally FIG. 4C shows the bandage 10 and the knee pressure pad 16 in the worn state.

The compressive knee bandage 10 of the compression garment set 4 shown in FIG. 4A substantially consists of an upper thigh part 52 and a lower leg part 53. Both parts enclose a patellar region 54. At the upper and lower end the bandage 10 further comprises a terminating edge 55 and 56. The knee bandage 10 is used to stabilize the joint. The bandage 10 preferably consists of a textile, in particular, stitched, tubular and compressive base body.

In addition to the bandage 10, the compression garment set 4 comprises the knee pressure pad 16. This is used substantially to reduce swellings in the area of the knee and the patella. This C- or O-shaped knee pressure pad 16 has, according to the invention, an adhesive surface 27 on the side 31 directed towards the wearer in the wearing position. The knee pressure pad 16 can thus be positioned in a detached manner, i.e. independently of the bandage 10 on the skin and the body part of a wearer and can be detachably fixed there. As in the exemplary embodiments previously, the pressure pad 16 preferably consists of a support film to which a pressure pad element 24 is attached. The pressure pad element 24 is here also preferably formed from a silicone with an adhesive surface so that the pressure pad element 24 itself forms the adhesive surface 27. On the side 31 directed towards the wearer in the wearing position the pressure pad element 24 preferably has a substantially flat or slightly concavely curved surface. The outer side of the pressure pad 16 on the other hand is here configured to be convexly curved.

In FIG. 4B the knee pressure pad 16 is now attached to the knee of the wearer. For this purpose the pressure pad 16 which has the adhesive surface 27 on the side 31 directed towards the wearer in the wearing position, is positioned in the area of the patella 54 and fixed therewith slight pressure, on the body part, in particular on the skin of the wearer. Due to the preferably slightly sticky, adhesive, in any case self-adhesive surface, the pressure pad 16 sticks to the skin of the wearer without external assistance.

FIG. 4C now illustrates a worn state in which the compression article, namely the knee bandage 10 of the compression garment set 4 is put on the leg of the wearer. The thigh part 52 with the termination 55 of the bandage 10 comes to rest in the area of the thigh, the lower leg part 53 with the termination 56 comes to rest in the area of the lower leg. The compressive bandage 10 in this case applies pressure to the leg of the wearer. In addition, the compressive bandage 10 covers the pressure pad 16 and also applies pressure to this. As a result, swellings, in particular in the region of the knee and the patella, are reduced. Thanks to the invention it is now no longer necessary to pull the knee bandage simultaneously with an incorporated pressure pad, as is known from the prior art, jointly along the leg of a wearer into a wearing position, namely into a knee area. The ease of putting on and taking off the compression garment set 4 according to the invention is thus made considerably easier compared with the already known solutions, in particular knee bandages.

FIGS. 5A to 5C show a further exemplary embodiment of the compression garment set 5 according to the invention with a compression article configured as a compressive glove 11 and a hand pressure pad 17. In FIG. 5A the set 5 is again shown in the unworn state. In FIG. 5B the hand pressure pad 17 is positioned on the hand of a wearer and fixed there. FIG. 5C finally shows the glove 11 and the hand pressure pad 17 in the worn state.

The compressive glove 11 of the compression garment set 5 shown in FIG. 5A consists of a compressive base body which surrounds the hand, in particular the inner side of the hand and also the back of the hand 63, as well as several finger sections 57 to 61. The preferably also compressive finger sections 57 to 61 can be configured to be open at their ends, as shown. However, it is also feasible that these are closed and thereby completely cover the several fingers of the wearer. Alternatively the glove can also be formed without finger sections. At the opposite end of the base body this has a terminating edge 62 or alternatively a collar section. The compressive glove 11 is preferably used for oedema therapy in the area of the hand. In this case, the glove 11 in particular ensures an optimal backflow of lymph fluid from the tissue of the hand and thus prevents this from accumulating in the hands and in the fingers. In this case, the glove 11 preferably consists of a textile, tubular and compressive knitted fabric.

The hand pressure pad 17 which is also part of the compression garment set 5 is preferably configured to be pad-shaped here. This serves to reduce swellings in the area of the hand, in particular in the area of the back of the hand 63. This hand pressure pad 17 now also has, according to the invention, an adhesive surface 28 on the side 31 directed towards the wearer in the wearing position. In contrast to the previous exemplary embodiments, the adhesive surface 28 of the pressure pad 17 is now formed by at least one adhesive layer 29 applied to the pressure pad 17. The pad-shaped pressure pad 17 itself is here also formed from an elastic plastic material. The hand pressure pad 17 can be positioned by means of the adhesive layer 29 in a detached manner, i.e. independently of the glove 11 on the hand of a wearer and fixed detachably there. In order to now be able to adapt the side of the hand pressure pad 17, the pressure pad 17 additionally has one or more cutting markings 32. It is thus possible to adapt the pressure pad 17 in terms of its shape and size individually to the hand, in particular to the back of the hand 63 of a wearer. The geometrical configuration of the pressure pad will be discussed in further detail in FIGS. 8A to 8C.

In FIG. 5B the hand pressure pad 17 is now attached to the hand of the wearer. For this purpose, the pressure pad 17 which has the adhesive surface 28 on the side 31 directed towards the wearer in the wearing position is positioned in the area of the back of the hand 63 and there fixed to the hand of the wearer with light pressure. As a result of the preferably slightly sticky layer 29 the pressure pad 17 sticks to the hand of the wearer without external assistance.

FIG. 5C now shows a worn state in which the glove 11 of the compression garment set 5 is put on the hand of the wearer. The compressive glove 11 with the plurality of finger sections 57 to 61 and the terminating edge 62 hereby applies pressure to the hand, in particular to the back of the hand 63 and thus to the pressure pad 17 which has already been fixed to the hand of the wearer by the adhesive surface 28, in particular adhesive layer 29, arranged on the side 31 directed towards the wearer in the wearing position. Swellings, in particular in the area of the back of the hand 63 are thus reduced. As has already been mentioned previously, in this exemplary embodiment also it is not necessary to pull the compression article 11 together with pressure pad 17 over the hand of a wearer which makes the ease of putting on and taking off the compression garment set significantly easier.

Finally FIGS. 6A to 6C show a further exemplary embodiment of the compression garment set 6 according to the invention. In this case, the compressive article is configured as compressive waistcoat 12. The pressure pad is formed here as thorax pressure pad 18. In FIG. 6A the set 6 is shown in an unworn state. In FIG. 6B the thorax pressure pad 18 is positioned on the upper body of a wearer and fixed there. FIG. 4C finally shows the compressive waistcoat 12 and the thorax pressure pad 18 in the worn state.

As shown in FIG. 6A, the compression article of the compression garment set 6 is configured as a compressive waistcoat 12. The preferably sleeveless waistcoat 12 here substantially consists of a base body to which preferably at least one closure 64, in particular a zip fastener, is attached for opening and closing the waistcoat 12. Preferably a waistband section 67 is provided on the base body at the lower edge of the waistcoat 12. In order to now be able to apply pressure or compression to the thorax, the waistcoat 12 has at least one, preferably several compression zones 65, 66. These zones are preferably fabricated from a less elastic material than the remaining base body of the waistcoat 12 which is preferably fabricated from a substantially elastic woven fabric, preferably textile woven fabric. The waistcoat 12 can here be configured as preferably multi-layered, in particular to form the plurality of compression zones 65 and 66.

The thorax pressure pad 18, which is also part of the compression garment set 6 and serves to reduce swellings in the area of the thorax has an oval shape here. On the side 31 directed towards the wearer in the wearing position this preferably has a substantially concavely curved surface. The outer side of the pressure pad 18 on the other hand is configured to be convexly curved here. This thorax pressure pad 18 also has, according to the invention, an adhesive surface 27 on the side 31 directed towards the wearer in the wearing position so that this can be positioned in a detached manner, i.e. independently of the waistcoat 12, on the skin and the thorax of a wearer and fixed detachably there. As previously in the exemplary embodiments in some cases, the pressure pad 18 also preferably consists of a support film to which a pressure pad element 25 is attached. The pressure pad element 25 is here preferably formed of a silicone with an adhesive surface so that the pressure pad element 25 itself forms the adhesive surface 27.

In FIG. 6B the thorax pressure pad 18 is attached to the upper body of the wearer. This is accomplished by fixing the pressure pad 18, which has the adhesive surface 27 on the side directed towards the wearer in the wearing position, in the area of the upper body and fixing it there with light pressure. Due to the preferably slightly sticky layer 27 the pressure pad 18 adheres to the skin of the upper body.

FIG. 6C now shows the worn state in which the waistcoat 12 of the compression garment set 6 is placed on the thorax of the wearer. The waistcoat 12 closed by means of the closure 64 with the plurality of compression zones 65 and 66 thereby applies pressure to the thorax and to the pressure pad 18 which is positioned by means of the adhesive surface 27 on the side 31 on the thorax. Swellings in the thorax are thereby reduced.

FIGS. 7A to 7C now show the ankle pressure pad 13 of the first exemplary embodiment of the compression garment set 1, in particular from FIGS. 1A to 1C in detail.

FIG. 7A shows the L-shaped pressure pad 13 in plan view, i.e., from the side 30 facing away from the wearer. On this outer side the pressure pad 13 is convexly curved. This outer side 30 is here formed by the support element 19 of the pressure pad 13, in particular by the support film on which the pressure pad element 21 is arranged. The support film 19 here has a low-friction surface so that the pressure pad 13 has enhanced sliding properties on the side facing the compression article 7. Pulling on the compression article, in particular the leg stocking 7, is made significantly easier by the low-friction surface on the outer side 30 of the pressure pad 13.

FIG. 7B now shows the ankle pressure pad 13 from below, in particular from the side 31 facing the wearer. On this one side 31 directed towards the wearer in the wearing position, the pressure pad 13 has the adhesive surface 27 in order to be able to position the pressure pad 13 detached from the compression article 7 on the skin of a wearer. The adhesive surface 27 is hereby formed by the adhesive surface 26 of the pressure pad element 21. The side 31 is here formed by a flat surface.

FIG. 7C now shows the ankle pressure pad 13 in a sectional view along the line AA according to FIG. 7A. The outer side 20 is formed by the support film 19 to which the pressure pad element 21 is attached. As already mentioned previously, this consists of an elastic plastic material, in particular of a silicone so that the pressure element 21 itself with the adhesive surface 26 forms the at least one adhesive surface 27 on the side 31 facing the wearer. The side 30 facing away from the wearer in the wearing position is configured to be highly curved, in particular convex. A cover element 33 can now be detachably attached to the adhesive surface 27. The adhesive surface 27 of the pressure pad 13 is thereby protected from contaminants in an exposed state. The detachable cover element 33 is preferably configured as a plastic film which covers the adhesive surface 27.

Not shown but preferably also part of the compression garment set 1 according to the invention is a means for cleaning the adhesive surface 27 so that the at least one pressure pad 13 can be reused. The means is preferably configured in such a manner that it releases oil and grease contaminants, dust, dirt, make-up, skin flakes, skin particles and hairs from the adhesive layer 27 without damaging the adhesive layer 27 in so doing.

Figure 8C:
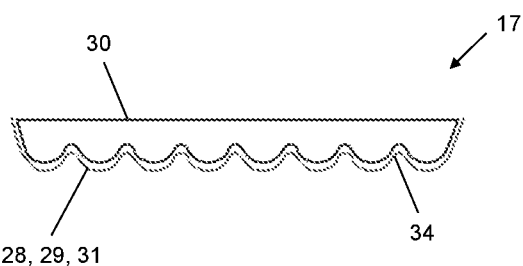

FIGS. 8A to 8C finally show the hand pressure pad 17 of the fifth exemplary embodiment of the compression garment set 5 according to the invention, in particular from FIGS. 5A to 5C in detail.

FIG. 8A shows the pad-shaped pressure pad 17 in plan view, i.e. from the side 30 facing the wearer. As can be seen, on this side 30 the pressure pad 17 has one or several cutting markings 32 in order to be able to adapt the size of the hand pressure pad 17 individually to the size of the back of a hand. The pad-shaped pressure pad 17 itself is also formed of a plastic material here.

FIG. 8B now shows the underside of the pressure pad 17, namely the side 31 facing a wearer. On this side 31 the hand pressure pad 17 has the adhesive surface 28. According to this exemplary embodiment, the adhesive surface 28 of the pressure pad 17 is formed by at least one adhesive layer 29 attached to the pressure pad 17, whereby the pressure pad 17 can be positioned in a detached manner, i.e. independently from a glove on the hand of a wearer and can be detachably fixed there. In order to now reduce swellings in the area of the hand, in particular in the area of the back of the hand, the pressure pad 17 has several recesses 34 on the side 31. The recesses 34 serve to form one, preferably several transport channels 34, in particular for the removal of lymph fluid, below the pressure pad 17 in the wearing position.

FIG. 8C now shows the hand pressure pad 17 in a sectional view along the line BB according to FIG. 8A. As can be seen, the side 30 facing away from the wearer in the wearing position is configured to be substantially flat. On the opposite side 31, with the adhesive surface 28 in the form of an additional adhesive layer 29 which is attached or applied to the pressure pad 17, the pressure pad 17 has a plurality of recesses 34, in particular in this exemplary embodiment seven. The recesses 34 and the inner side 31 of the pressure pad 17 hereby forms a preferably wave-shaped surface or adhesive surface 28 with a plurality of transport channels 34 for lymph fluid. Alternatively other geometrical configurations of the recesses 34 are naturally also feasible. For example, these can be v- or u-shaped. Alternatively spaced-apart pressure pad elements can also be provided. The adhesive layer 29 can also consist of several sections.

The invention is not restricted to the exemplary embodiments described but comprises all designs which apply or include the fundamental, corresponding functional principle of the invention. Furthermore, all the features of all the described and depicted exemplary embodiments can be combined with one another.

The invention claimed is:

1. A compression garment set for applying compression to a body part consisting of:
   at least one compression article and at least one pressure pad pertaining to the compression article,
   wherein in a wearing position of the compression garment set the at least one pressure pad comes to lie under the at least one compression article between the at least one compression article and a skin of a wearer, wherein the at least one pressure pad has at least one adhesive surface on a side directed towards the wearer in a wearing position such that the at least one pressure pad is positionable on the skin of the wearer detached from the at least one compression article, and
   wherein the at least one pressure pad consists of silicone with an adhesive surface such that the at least one pressure pad itself forms at least one adhesive surface, the at least one adhesive surface covers an entire surface of the at least one pressure pad.

2. The compression garment set of claim 1, wherein the at least one pressure pad has at least one support element for the at least one pressure pad attached thereto on a side facing away from the wearer in the wearing position.

3. The compression garment set of claim 2, wherein the at least one support element is fabricated from a support film having a low-friction surface on an outer side so that the pressure pad has enhanced sliding properties on a side facing the compression article.

4. The compression garment set of claim 2, wherein the at least one pressure pad has at least one recess on the side directed towards the wearer in the wearing position or wherein a plurality of adjoining or spaced-apart pressure pads are attached to the support element to form at least one transport canal for lymph fluid in the wearing position below the pressure pad.

5. The compression garment set of claim 1, wherein the geometry of the at least one pressure pad is adapted to an anatomy of the body part in the wearing position on the side directed towards the wearer in the wearing position.

6. The compression garment set of claim 5, wherein the pressure pad formed on the side directed towards the wearer in the wearing position is substantially flat, convex, or concavely curved.

7. The compression garment set of claim 1, wherein the at least one pressure pad consists of an elastic or plastically deformable plastic material.

8. The compression garment set of claim 1, wherein the at least one adhesive surface is formed by an adhesive layer applied to the at least one pressure pad.

9. The compression garment set of claim 1, wherein the at least one pressure pad is substantially convexly curved on a side facing away from the wearer in the wearing position.

10. The compression garment set of claim 1, wherein the at least one pressure pad has one or more cutting markings such that the at least one pressure pad can be individually adapted in its shape.

11. The compression garment set of claim 1, further comprising at least one cover element configured to be detachably attached to the at least one adhesive surface of the at least one pressure pad so that the adhesive surface of the at least one pressure pad in an exposed state is protected from contaminants.

12. The compression garment set of claim 1, further comprising a means for cleaning the adhesive surface such that the at least one pressure pad is reuseable.

13. The compression garment set of claim 1, wherein the at least one compression article is a stocking, a sock, a toe cap, a glove, a bandage, an adjustable compression textile, a waistcoat, or a compressive element of an orthesis.

14. The compression garment set of claim 1, wherein compressive pressures generated by the compression article are between 5 and 60 mm Hg.

15. A compression garment set for applying compression to a body part consisting of:
   at least one compression article and at least one pressure pad pertaining to the at least one compression article,
   wherein in a wearing position of the compression garment set the at least one pressure pad comes to lie under the at least one compression article between the at least one compression article and a skin of a wearer, wherein the at least one pressure pad has at least one adhesive surface on a side directed towards the wearer in the wearing position so that the at least one pressure pad is positionable on the skin of the wearer detached from the compression article, and wherein the at least one adhesive surface is formed by an adhesive layer applied to the at least one pressure pad, the at least one adhesive surface covers an entire surface of the at least one pressure pad.

16. The compression garment set of claim 15, wherein the pressure pad has one or more cutting markings such that the pressure pad is individually adaptable in its shape.

17. The compression garment set of claim 15, further comprising a means for cleaning the adhesive surface such that the at least one pressure pad is reuseable.

18. A compression garment set for applying compression to a body part consisting of:

at least one compression article and at least one pressure pad pertaining to the compression article, wherein in a wearing position of the compression garment set the at least one pressure pad comes to lie under the compression article between the compression article and a skin of a wearer, wherein the at least one pressure pad has at least one adhesive surface on a side directed towards the wearer in the wearing position such that the at least one pressure pad is positionable on the skin of a wearer detached from the at least one compression article, and wherein the at least one adhesive surface covers an entire surface of the pressure pad, and a means for cleaning the at least one adhesive surface such that the at least one pressure pad is reusable.

19. The compression garment set of claim 18, wherein the at least one pressure pad has one or more cutting markings such that the at least one pressure pad is individually adaptable in its shape.

20. The compression garment set of claim 18, wherein the at least one adhesive surface is formed by an adhesive layer applied to the at least one pressure pad.

* * * * *